(12) United States Patent  
Vongphakdy et al.

(10) Patent No.: US 8,597,276 B2  
(45) Date of Patent: Dec. 3, 2013

(54) IMPLANT DELIVERY SYSTEM WITH INTERLOCKED RX PORT ORIENTATION

(75) Inventors: Khamla Vongphakdy, Big Lake, MN (US); Huisun Wang, Maple Grove, MN (US); Adel Hashw, Eden Prairie, MN (US); Lixiao Wang, Long Lake, MN (US)

(73) Assignee: Covidien LP, Mansfield, MA (US)

( * ) Notice: Subject to any disclaimer, the term of this patent is extended or adjusted under 35 U.S.C. 154(b) by 1059 days.

(21) Appl. No.: 11/433,328

(22) Filed: May 12, 2006

(65) Prior Publication Data

US 2006/0259120 A1 Nov. 16, 2006

Related U.S. Application Data

(60) Provisional application No. 60/680,400, filed on May 12, 2005, provisional application No. 60/680,791, filed on May 13, 2005, provisional application No. 60/738,764, filed on Nov. 21, 2005.

(51) Int. Cl.  
  *A61M 25/00*  (2006.01)
(52) U.S. Cl.  
  USPC ........................................................ 604/523
(58) Field of Classification Search  
  USPC .................... 604/523, 198, 534, 535  
  See application file for complete search history.

(56) References Cited

U.S. PATENT DOCUMENTS

| | | | | |
|---|---|---|---|---|
| 5,490,837 | A | * | 2/1996 | Blaeser et al. ............ 604/103.11 |
| 5,683,451 | A | * | 11/1997 | Lenker et al. ................ 623/1.11 |
| 2003/0028235 | A1 | | 2/2003 | McIntosh et al. |
| 2004/0236406 | A1 | | 11/2004 | Gregorich |
| 2005/0149159 | A1 | * | 7/2005 | Andreas et al. .............. 623/1.11 |
| 2008/0262506 | A1 | * | 10/2008 | Griffin et al. ................ 606/108 |

FOREIGN PATENT DOCUMENTS

WO   WO 99/49929 A1   10/1999

* cited by examiner

*Primary Examiner* — Bhisma Mehta  
*Assistant Examiner* — Bradley Osinski  
(74) *Attorney, Agent, or Firm* — Alana T. Bergman, Esq

(57) ABSTRACT

A medical implant delivery system maintains an orientation between a guidewire lumen of an inner member of the system and a rapid-exchange port in an outer member. The medical device is disposed intermediate the inner and outer members and in friction or pressure-fit contact with the outer member. Once the guidewire lumen of the inner member and the rapid exchange port of the outer member are oriented, the friction or pressure-fit operates to maintain the orientation until deployment of the medical implant. Orientation is further maintained by a telescoping coupling of the guide wire lumen with the rapid exchange port.

16 Claims, 9 Drawing Sheets

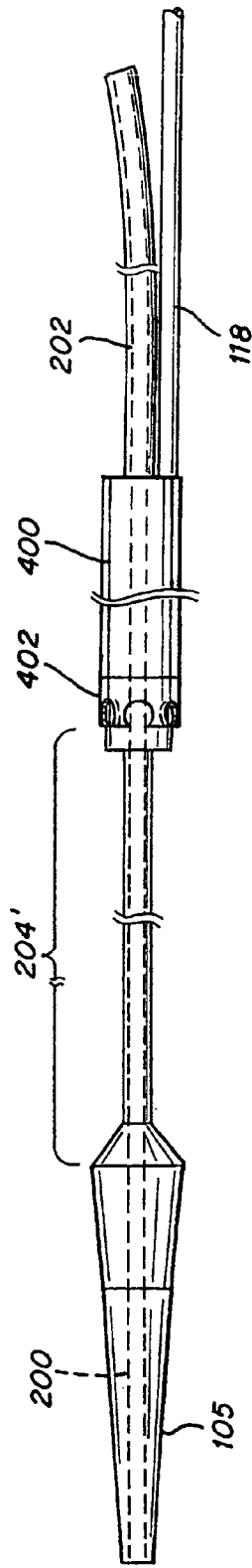
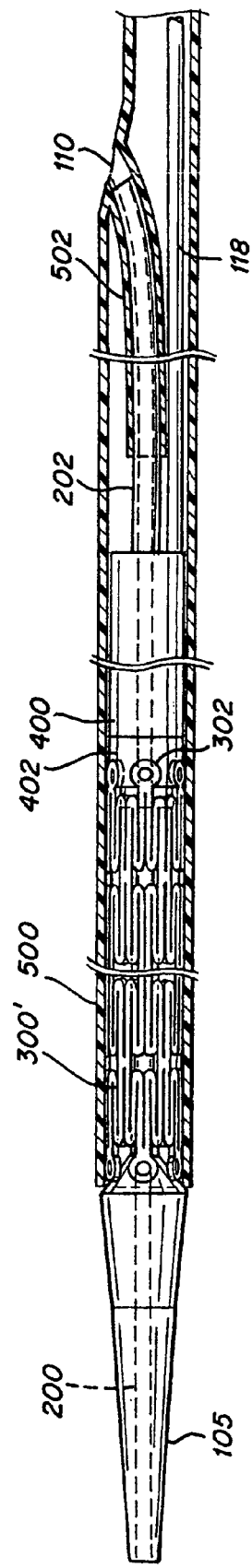
Fig. 4A
Fig. 4B

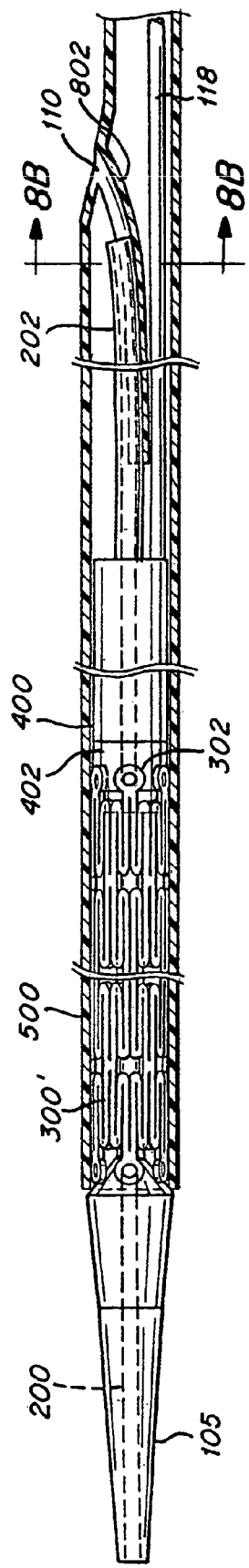
Fig. 8A
Fig. 9
Fig. 8B

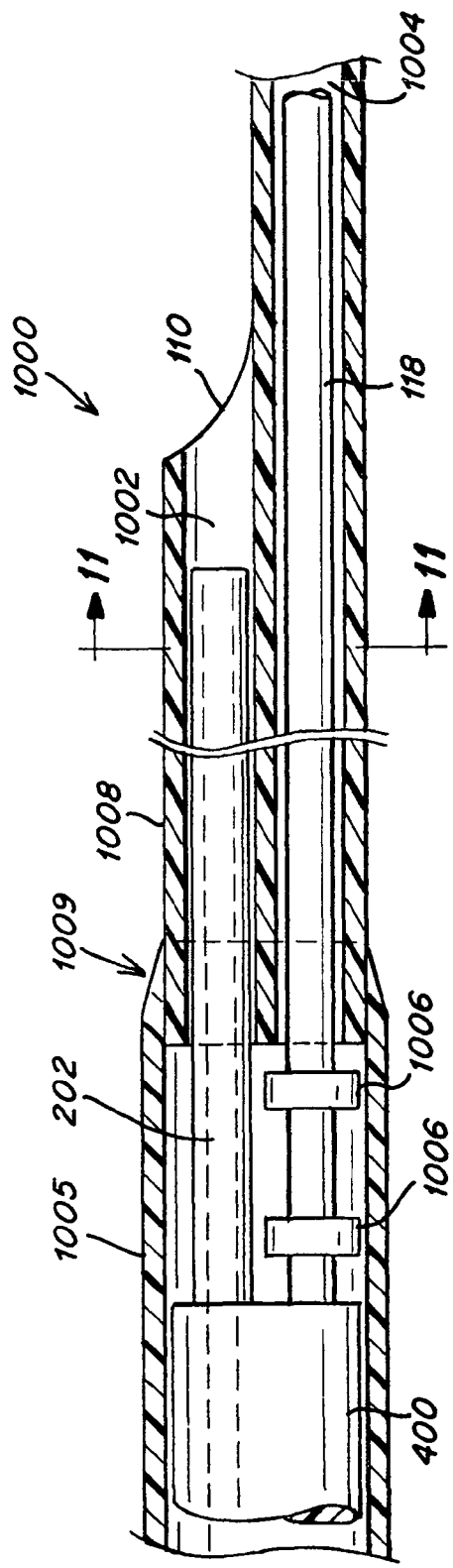
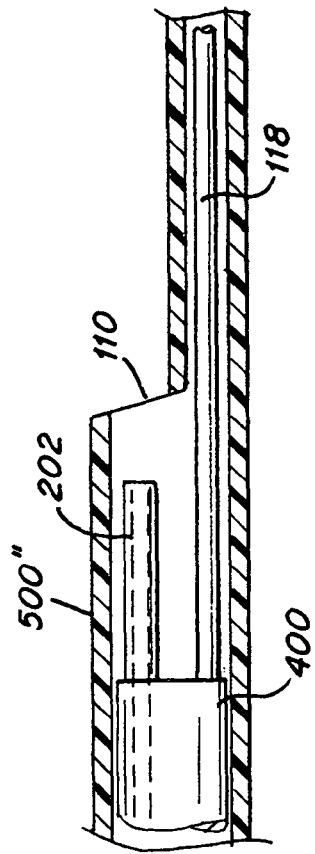
Fig. 10
Fig. 12
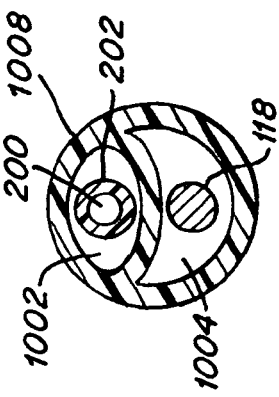
Fig. 11

IMPLANT DELIVERY SYSTEM WITH INTERLOCKED RX PORT ORIENTATION

RELATED APPLICATIONS

This application claims priority to U.S. Provisional Patent Application Ser. No. 60/680,400, filed May 12, 2005 by Khamla Vongphakdy and Huisun Wang, U.S. Provisional Patent Ser. No. 60/738,764, filed Nov. 21, 2005 by Khamla Vongphakdy, Adel Hashw, Lixiao Wang and Huisun Wang, and U.S. Provisional Patent Application Ser. No. 60/680,791, filed May 13, 2005 by Khamla Vongphakdy and Huisun Wang, the entire subject matters of which are hereby incorporated by reference.

FIELD OF THE INVENTION

The present invention pertains to a system for delivering an implant to a site in a body lumen. More particularly, this invention pertains to a rapid exchange-type delivery system for a self-expandable implant such as a stent.

BACKGROUND OF THE INVENTION

Stents are widely used for supporting a lumen structure in a patient's body. For example, a stent may be used to maintain patency of a coronary artery, other blood vessel or other body lumen. One or more stents may be placed in a vascular or non-vascular passage or conduit such as an artery, vein, graft, ureter, urethra, bronchus, esophagus, or other passage. Stents can be placed as a carrier for delivering medications for diagnostic or therapeutic purposes, to facilitate flow of liquids, air, or other substances, or for other reasons as is known in the art.

A stent is typically a metal, tubular structure, although polymer stents are known. Stents can be permanent enduring implants, or can be bioabsorbable at least in part. Bioabsorbable stents can be polymeric, bio-polymeric, ceramic, bio-ceramic, or metallic, and may elute over time substances such as drugs. In some instances, a stent is passed through the body lumen in a collapsed state. At the point of an obstruction, or other deployment site in the body lumen, the stent is expanded to its expanded diameter for its intended purpose.

In certain stent designs, the stent is an open-celled tube that is expanded by an inflatable balloon at the deployment site. Another type of stent is of a "self-expanding" type. A self-expanding stent does not use a balloon or other source of force to move from a collapsed state to an expanded state. An example of a self-expanding stent is a coil structure that is secured to a stent delivery device under tension in a collapsed state At the deployment site, the coil is released so that the coil can expand to its enlarged diameter. Another type of self expanding stent is an open-celled tube made from a self-expanding material, for example, the Protege GPS stent from ev3, Inc. of Plymouth, Minn. Some types of self-expanding stents are made of so-called shape-memory metals such as nitinol. Shape-memory metal stents can self expand when thermomechanically processed to exhibit superelastic material properties. Such shape-memory stents can also self-expand through use of a pre-programmed shape memory effect. Stents processed to exhibit a shape memory effect experience a phase change at the elevated temperature of the human body. The phase change results in expansion of the stent from a collapsed state to an enlarged state.

As is known, a stent is delivered to a deployment site by a stent delivery system. The stent is mounted on a distal end of such a system, the system is maneuvered within a patient's lumen, conduit, or passage and expanded and released at the desired location. There are two main types of stent delivery systems: over-the-wire (OTW) systems and rapid-exchange (RX) systems. In an OTW system a guidewire, used to facilitate navigation or tracking of the stent delivery system through the body, is slideably contained within the full length of the stent delivery system. In an RX system the guidewire is slideably contained within a short distal length of the stent delivery system. RX systems provide certain advantages as compared to OTW systems. RX stent delivery systems use short (typically 170 cm) guidewires which can be handled by one operator, whereas OTW stent delivery systems require long (typically 320 cm) guidewires which must be handled by two operators, increasing procedural cost and complexity.

While an RX system may provide advantages over an OTW system, the RX system presents some issues of its own that must be considered. For example, it is important for the stent delivery system to slide easily over the guidewire so that the stent can be easily tracked over the guidewire to the intended stent deployment site. If the components of the stent delivery system are not properly aligned there can be friction against, or entanglement with, the guidewire. In some situations, guidewire interaction issues such as these can prevent the stent delivery system from tracking to the intended stent deployment site, or can even prevent deployment of the stent after the site is reached.

Because of the tortuous pathway in the body and the torqueing of the delivery system during advancement to the deployment site, it is important to maintain an orientation between a guidewire lumen located within an inner member in a medical delivery system and an RX port. If this orientation is lost, it may not be possible to mount the delivery system on the guidewire or it might take too much time. Any delays may be detrimental to the patient. Further, if the needed orientation is lost, it may not be possible to track the stent to the intended deployment site, or to deploy the stent.

Accordingly, a need exists for a medical implant delivery system which is capable of maintaining proper orientation between coaxially slidable members of the system, particularly with reference to the rapid exchange guide wire lumen and the deployable device carried by the delivery system.

SUMMARY OF THE INVENTION

A medical implant delivery system maintains an orientation between a guidewire lumen of an inner member of the system and a rapid-exchange port in an outer member. The medical device is disposed intermediate the inner and outer members and in friction or pressure-fit contact with the outer member. Once the guidewire lumen of the inner member and the rapid exchange port of the outer member are oriented, the friction or pressure-fit operates to maintain the orientation until deployment of the medical implant. Orientation is further maintained by the telescoping coupling of the guide wire lumen with the rapid exchange port.

According to one aspect of the present invention, a system for delivering a medical device within a body lumen compriss: a tubular catheter having proximal and distal ends and comprising an outer shaft member slidably disposed about an inner shaft member; a medical device disposed intermediate the inner and outer shaft members; a guide wire lumen extending at least partially through each of the inner shaft member and the outer shaft member, the guide wire lumen opening exterior of the outer shaft member at a location distal of the catheter proximal end; and an alignment mechanism maintaining alignment of the guide wire lumen relative to the outer shaft member and the inner shaft member.

According to a second aspect of the present invention, a system for delivering a medical device within a body lumen comprises: a tubular inner shaft member having a proximal end and a distal end and defining an inner shaft guide wire lumen extending at least partially therethrough; a tubular outer shaft member having a proximal end and a distal end and defining an outer shaft guide wire lumen extending at least partially therethrough and opening exterior of the outer shaft member at a location proximal of the distal end of the outer shaft member, the outer shaft member slidably disposed about the inner shaft member; a medical device disposed intermediate the inner and outer shaft members; and an alignment mechanism maintaining rotational alignment and communication between the portions of the guide wire lumen extending at least partially through the inner shaft member and the outer shaft member.

According to a second aspect of the present invention, a system for delivering an implant, the system comprises: an inner member comprising an implant receiving portion, and a guidewire lumen extending through the inner member, and a guidewire lumen extension portion; and an outer member comprising a port opening and a port opening extension portion coupled to the guidewire lumen extension portion, the outer member disposed about the inner member and sized to provide friction contact with an implant to be mounted on the inner member, wherein the inner member is configured to be rotationally fixed with respect to the outer member as a function of a friction contact of an implant to be mounted on the inner member against the outer member.

BRIEF DESCRIPTION OF THE DRAWINGS

The above and further advantages of the invention may be better understood by referring to the following description in conjunction with the accompanying drawings in which:

FIGS. 4A-C are schematic drawings of portions of a delivery system according to one embodiment of the present invention;

FIGS. 8A-8B are schematic drawings of a portion of a delivery system according to another embodiment of the present invention;

FIG. 9 is a schematic cross-sectional drawing of axial ridges provided in one embodiment of the present invention;

FIG. 10 is an alternate embodiment of the present invention where the delivery system comprises a bitumen structure;

FIG. 11 is a cross-sectional drawing of a portion of the delivery system shown in FIG. 10; and FIG. 12 is an alternate embodiment of the delivery system according to the present invention.

DETAILED DESCRIPTION

Figure 1B:
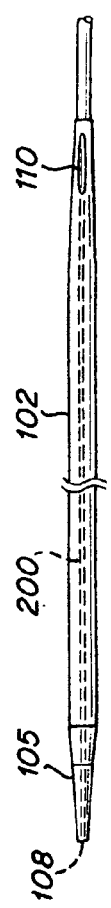
FIGS. 1A-B are schematic drawings of a delivery system.

The invention is herein described, by way of example only, with reference to the accompanying drawings. It is stressed that the particulars shown are for purposes of illustrative discussion of the various embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

It is to be understood that the invention is not limited to the details of construction and the arrangement of the components set forth in the following description or illustrated in the drawings. The invention is capable of other embodiments or of being practiced or carried out in various ways. Also, it is to be understood that the phraseology and terminology employed herein are for the purpose of description and should not be regarded as limiting.

Further, certain features of the invention, which are, for the sake of clarity, described in the context of separate embodiments, may also be provided in combination in a single embodiment. Conversely, various features of the invention, which are, for brevity, described in the context of a single embodiment, may also be provided separately or in any suitable subcombination.

Figure 1A:
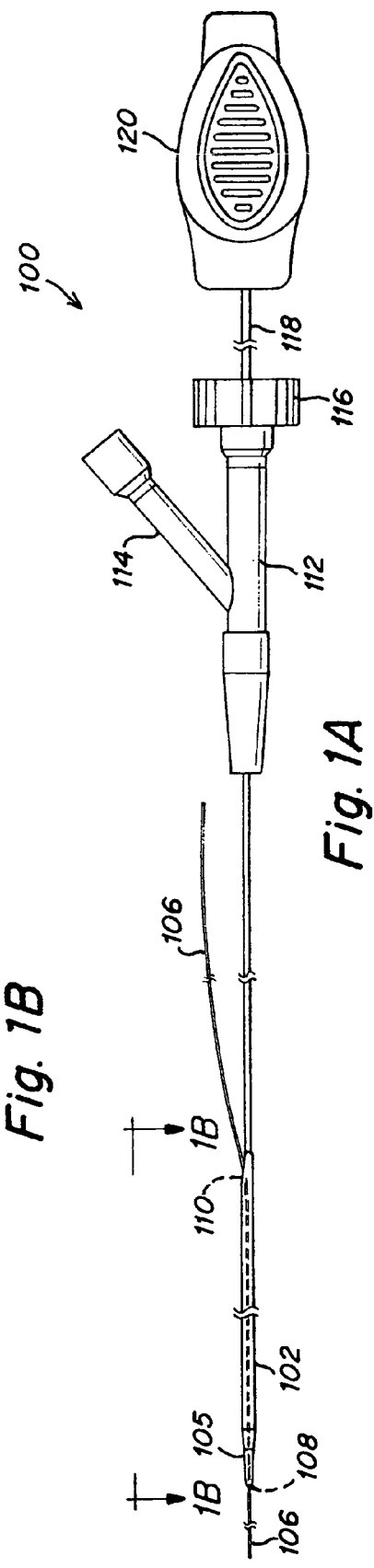

An RX stent delivery system 100, as shown in FIG. 1A, comprises an outer tubular member 102 and an inner tubular member 104 disposed within, only a portion of which is shown. Stent delivery system 100 further comprises a manifold housing 112 coupled to the outer member 102. The housing 112 includes a sidearm 114 and a locking member 116. A push wire 118 has a distal end coupled to the inner member 104 and a proximal end coupled to a handle 120. As used herein references to distal and proximal portions of the system are with respect to the user's perspective, i.e., with proximal being located closer to the user and distal being located farther from the user.

The inner member 104 and outer member 102 are axially slideable relative to one another. The push wire 118 and housing 112 are used to facilitate movement of the inner member 104 relative to the outer member 102. The locking member 116 can be operated to couple the housing 112 to the push wire 118 in order to allow inner member 104 and outer member 102 to move in unison.

The outer member 102, in one embodiment, may be made of kink resistant extruded polymer tubing with adequate strength and lubricity for unsheathing a stent. Polymers such as nylon, PEBAX, polyethylene, or polyester may be used. Alternatively, thermoset polymers, such as polyimide or braid reinforced polyimide may be used. In some embodiments, the distal portion of the outer member 102 may be transparent to allow inspection of a stent or other components within. The inner member 104, in one embodiment, may be made of a flexible and kink resistant polymer such as metallic braid reinforced polyimide, although polymers such as nylon, PEBAX, polyethylene, or polyester may also be used. Inner member 104 further comprises a tip member 105 that made be made of a soft flexible material. The push wire 118, in one embodiment, may be constructed of metal. In another embodiment, the proximal end of the push wire 118 comprises stainless steel tubing while the distal portion of push wire 118 comprises of metal wire. This combination provides adequate column strength throughout, good bending resistance proximally, and good bending flexibility distally. The housing 112 and the locking member 116 may be each comprise polycarbonate, polystyrene, or other materials, and a sealing gland (not shown) may be used in cooperation with the housing 112 and the locking member 116 to create a fluid seal and mechanical lock between the housing 112, the locking member 116, and the push wire 118, in a manner known in the art. In the illustrative embodiment, locking member 116 may be implemented with a rotatably actuable clamp or gland that can frictionally engage push wire 118. The handle 120 may comprise polycarbonate, polystyrene, nylon, or other materials. Alternate materials for these components, as are generally well known in the art, can be substituted for any of the non-limiting examples listed above provided the functional requirements of the component are met Prior to advancing the stent delivery system 100 through a body lumen, a guidewire 106 is first passed through the body lumen to or beyond the deployment site. The delivery system 100, including the inner member 104 and the outer member 102, collectively define a guidewire lumen 200, which extends from a distal guidewire port 108 at the distal end of tip member 105, adapted to receive the guidewire 106, proximally to an RX port 110 located proximally of the distal guidewire first port 108, and which serves as an exit for the guidewire 106.

As shown in FIG. 1B, which is a partial top view of the system 100 as seen along line 1B-1B of FIG. 1, the RX port 110 extending through the wall of outer member 102, in one embodiment, may have an oval or teardrop shape to accommodate the movement of the system 100 along the guidewire 106. The RX port 110 maybe implemented with a "skive" in the sidewall of the outer member 102. By providing the RX port 110 as a skive, the guidewire 106 is able to maintain a flatter profile with respect to a central axis of the system. Advantageously, the guidewire 106 is kept at a shallower exit angle, in the range of 1° to 4°, as it leaves the RX port 110 which reduces the drag on the wire and also lowers the incidence of guidewire kinking.

The combined structure, i.e., the stent mounted on the stent delivery system, is loaded onto the guidewire 106 by inserting a proximal end of the guidewire 106 into the distal guidewire port 108, and then advancing the system 100 distally over the guidewire 106. The system is passed through the patient's lumen, over the guidewire 106, until the distal end of the delivery system 100 arrives distal to the deployment site within the body lumen. The delivery system 100 may include radio-opaque markers (not shown) to permit a physician to visualize positioning of the stent under fluoroscopy prior to deployment. For example, a platinum/iridium alloy band may be attached to the inner member 104 at a central axial location relative to the compressed stent 300. A solution of contrast media may be injected through the sidearm 114 to assist in visualization of the patient's lumen or of the system position before, during, or after system advancement or stent deployment.

Locking member 116 is typically tightened to limit axial motion between the inner member 104 and the outer member 102 during system advancement through the body and to prevent inadvertent stent deployment. At the deployment site, the locking member 116 is loosened (if previously tightened) and the outer member 102 is retracted proximally relative to the inner member 104 to expose the stent to the interior of the body lumen. Retraction may occur by holding handle 120 while simultaneously placing a retrograde or proximal force on the proximal end of housing 112. The exposed stent expands radially outward against the walls of the body lumen as outer member 102 is retracted until the stent is fully deployed. Following expansion of the stent, the inner member 104 is free to pass through the stent such that the delivery system 100 can be removed through the body lumen, returning over the guidewire 106, leaving the stent in place at the deployment site. The stent may be further processed such as, by way of example, post dilatation, to improve the wall apposition of the stent to the body lumen. Additional treatments or diagnostic procedures may be carried out, such as balloon dilations, stent deployments, ultrasound imaging, or other procedures as are known in the art, either before or after system advancement or stent deployment. At the end of the procedure(s) the guidewire 106 is withdrawn from the patient.

Figure 2A:
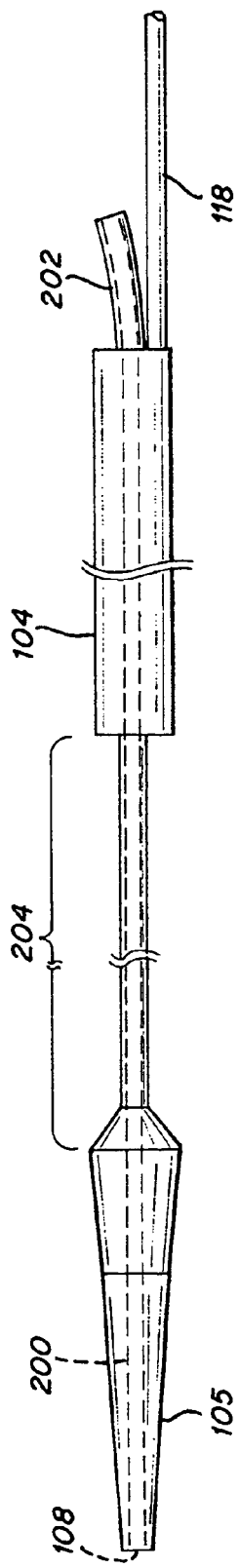
FIGS. 2A-C are schematic drawings of an inner member portion useable within the delivery system of FIGS. 1A-B.

As shown in FIG. 2A, the inner member 104 includes a guidewire lumen 200 running from the distal guidewire port 108 to a proximal portion of the inner member 104. A guidewire lumen extension 202 is provided to extend the guidewire lumen 200 beyond the proximal end of a main portion of the inner member 104. The guidewire lumen extension 202 may be, in one embodiment, made of flexible and kink resistant polymer such as metallic braid reinforced polyimide, although polymers such as nylon, PEBAX, polyethylene, or polyester may be used. The guidewire lumen extension 202 can be about 10 cm-40 cm in length, and in one embodiment, is about 25 cm in length. The guidewire lumen extension 202 has an inner diameter sized to allow low friction passage of the guidewire 106 therethrough and may have a wall thickness of 0.002"-0.010". Typically, the inner diameter of the guidewire lumen extension 202 may be 0.002"-0.006" greater than a nominal outer diameter of the guidewire 106. The push wire 118 is shown coupled to the inner member 104 near the proximal end thereof. A stent receiving portion 204, located substantially at the distal end of the inner member 104, is implemented, in the illustrative embodiment, as a reduced diameter section, to receive a stent. The stent receiving portion 204 can range from about 5 cm to 200 cm in length, and in some embodiments ranges from about 20 cm to about 90 cm. The depth of the stent receiving portion 204 will be equal to or slightly larger than a thickness of the stent 300, typically 0.002"-0.015".

The guidewire 106 may have an outer diameter in the range of 0.010"-0.038", nominally 0.014". The inner member 104 is dimensioned to allow low friction passage of the guidewire 106 within the guidewire lumen 200. The guidewire lumen 200 length can vary widely but desirably ranges from 5 cm to 50 cm in length. In one embodiment, the guidewire lumen 200 is approximately 30 cm in length. A size of the outer member 102 can range from about 10 Fr to about 3 Fr, where an outer member size of about 5 Fr is desirable for compatibility with currently popular guide catheter (not shown) dimensions. The outer member 102 length can be varied to suit the application of interest. Outer member lengths of 40 cm-200 cm have been found desirable. In one embodiment, an outer member length of about 145 cm has been found most effective.

Figure 2B:
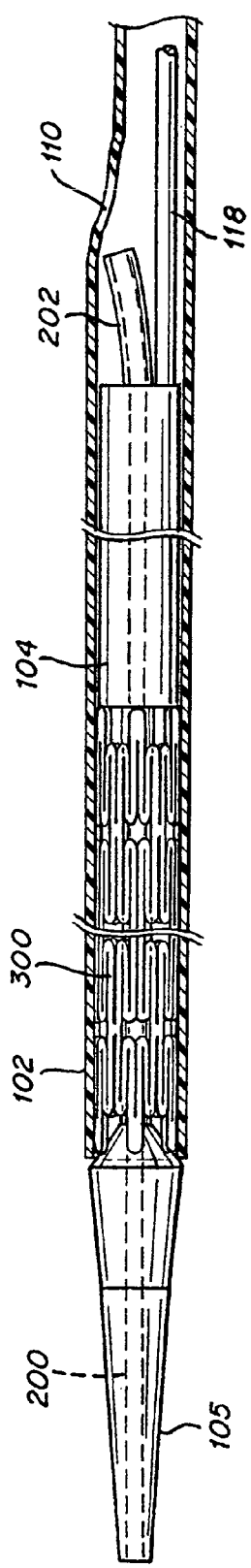

As shown in FIG. 2B, a self-expanding stent 300 is positioned on the inner member 104 substantially at the stent receiving portion 204. The stent 300 is positioned in its compressed form and held in place by the outer member 102, also referred to as an outer sheath. The stent 300 will expand to the extent of the inner diameter of outer member 102 while contained within the outer member.

As a non-limiting, representative example, the stent 300 may be a self-expanding, open-celled, tubular stent having a construction such as that shown in U.S. Pat. No. 6,132,461 and formed of a self-expanding, shape-memory or superelastic metal such as nitinol, or the like. The stent 300 may also be a coil stent or any other self-expanding stent.

When the system 100 is assembled with the inner member 104, the guidewire extension lumen 202 is oriented such that the guidewire 106 (not shown in FIG. 2B) will pass through the guidewire lumen 200 within the main portion of inner member 104, through guidewire extension lumen 202, and out RX port 110.

Figure 2C:
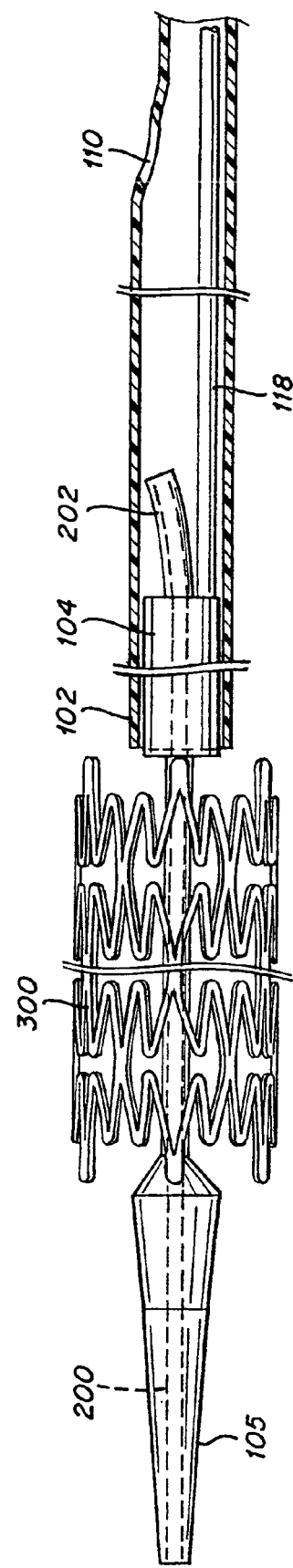

When the system 100 has been advanced to the location at which the stent 300 is to be placed, the stent 300 is released by operation of the push wire 118 and the manifold housing 112. Specifically, the outer member 102 is retracted proximally relative to the inner member 104, as described previously, thereby allowing the stent 300 to expand and release from the inner member 104, as shown in FIG. 2C. Once the stent 300 has expanded into place, the distal portion of the system 100 can be withdrawn back through the now-expanded stent 300.

Figure 3:
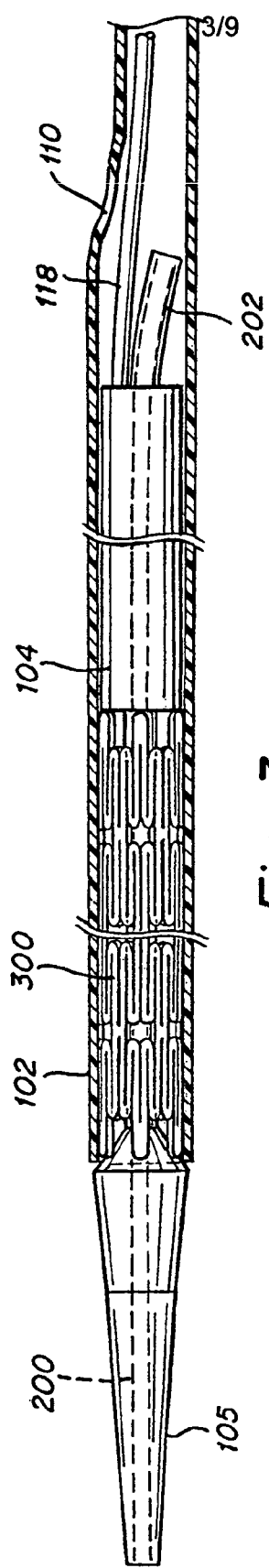
FIG. 3 is a schematic drawing of a rotated inner member portion of FIGS. 2A-C in the delivery system of FIG. 1.

The inner member 104 shown in FIGS. 2A-2C has a characteristic that, in some cases, can interfere with the device's proper operation. As the stent 300 has expanded to the extent allowed by the outer member 102, it is possible for the inner member 104 to rotate. In an OTW system, such rotation may not be an issue, however, for an RX system, the consequences are significant. As shown in FIG. 3, when the inner member 104 has rotated, the guidewire lumen extension 202 no longer aligns with the RX port 110. If the inner member 104 has rotated and the guidewire 106 is inserted during a procedure, precious time may be lost in trying to re-orient the lumen with the RX port 110. Further, the system 100 or the stent 300 may become damaged during attempts to re-align the system 100.

In order to prevent rotation and misalignment of the guidewire lumen extension 202 relative to RX port 110, one aspect of the present invention is directed to an interlocking inner member 400 including an interlock mechanism or portion 402, as shown in FIG. 4A. The interlocking inner member 400 has a structure that is similar to the non-interlocking inner member 104 in that there is a guidewire lumen 200 extending therethrough in addition to the guidewire lumen extension 202 and a push wire 118. In one embodiment of the present invention, a stent receiving portion 204' is provided in the interlocking inner member 400 to receive a stent. Dimensional and material aspects of these components are similar to the considerations discussed in relation to FIGS. 1 and 2.

The interlock mechanism 402 may have a structure similar to that which is described in commonly assigned U.S. Pat. No. 6,623,518 titled "Implant Delivery System With Interlock,", the subject matter of which is incorporated herein by reference in its entirety.

The interlock mechanism 402 includes structure or structures configured to couple to a stent disposed on the stent receiving portion 204' of the interlocking inner member 400. As shown in FIG. 4B, an interlocking stent 300' is disposed on the stent receiving portion 204' of the interlocking member 400. The interlocking stent 300' includes one or more interlocking tab portions 302 which couple with the interlock mechanism 402. When the interlocking stent 300' is positioned in its compressed or reduced diameter condition on the stent receiving portion 204', the interlocking tab portion 302 couples to the interlock mechanism 402, even as the interlocking stent 300' expands within its sheath. In one embodiment, the interlocking inner member 400 is formed of nylon although one of ordinary skill in the art will understand that materials with similar mechanical characteristics can be substituted.

In addition to the interlocking inner member 400, one aspect of the present invention provides an interlocking outer tubular member 500. Also as shown in FIGS. 4B and 4D, the interlocking outer member 500 comprises an RX port extension 502 to receive the guidewire lumen extension 202. The RX port extension 502, in one embodiment, may comprise a tube having a diameter large enough to receive the guidewire extension lumen 202. The RX port extension 502 can be made of flexible and kink resistant polymer such as nylon, PEBAX, polyethylene, or polyester, although metallic braid reinforced polymers may be used. In an alternate embodiment, as shown in FIG. 8A, the RX port extension 502 may comprise a ramp 802 to direct the guidewire lumen extension 202 to the RX port 110. The ramp 802, as shown in cross-sectional view of FIG. 8B as taken along line 8B-8B of FIG. 8A, supports and directs the guidewire lumen extension 202. In one embodiment, the ramp 802 is curved with a radius similar to that of the guidewire lumen extension 202 to provide better support. The choice of the lengths of the guidewire lumen extension 202 and ramp 802 provides the "telescoping" effect that maintains continuity of the guidewire lumen.

The interlocking outer tubular member 500, in one embodiment, may be made from a braid-reinforced polyester of tubular construction to resist kinking and to transmit axial forces along its length. The interlocking outer tubular member 500 may be constructed to permit varying degrees of flexibility along its length. The interlocking outer tubular member 500 may be provided with axial ridges 901, as shown in FIG. 9, along its inner lumen to increase contact with the stent to prevent stent rotation yet permit stent axial translation relative to the interlocking outer tubular member 500. The axial ridges 901 are positioned circumferentially around an inner circumference of the outer tubular member 500 and extend along at least a portion of the length of tubular member 500. The ridges 901 may or may not be uniformly distributed around the circumference. Further, the axial ridges 901 may have either a round or flat surface to contact the stent. Dimensional and material aspects of the interlocking outer tubular member 500 are similar to the considerations discussed in relation to FIGS. 1 and 2.

The interlocking stent 300' is urged against the inside diameter of the outer member 500 due to the self-expanding characteristics of the stent 300'. Further, the interlocking stent 300' is coupled to the interlock mechanism 402 of the interlocking inner member 400. As a result of the interlocking stent 300' being in outwardly urged relation to the outer member 500 and coupled to the interlock mechanism 402, the interlocking inner member 400 and the interlocking outer member 500 are rotationally fixed with respect to one another.

One of ordinary skill in the art will understand that the force of the interlocking stent 300' against the interlocking outer member 500 is sufficient to prevent the rotation of the interlocking inner member 400 relative to the interlocking outer member 500 while still allowing for a slidable movement between the interlocking inner member 400 and the outer member 500.

Once initially oriented, for example, during the manufacturing process, the delivery system, as shown in FIG. 4B, will maintain the orientation of the guidewire lumen extension 202 in the RX port extension 502. Handling of the delivery system, in accordance with the embodiments shown in FIG. 4B, during normal packaging, shipping, and operating procedures, will not result in a discontinuity in the guidewire lumen 200, or in a substantial rotation of the guidewire lumen extension portion 202 relative to the RX port extension 502.

Figure 4C:
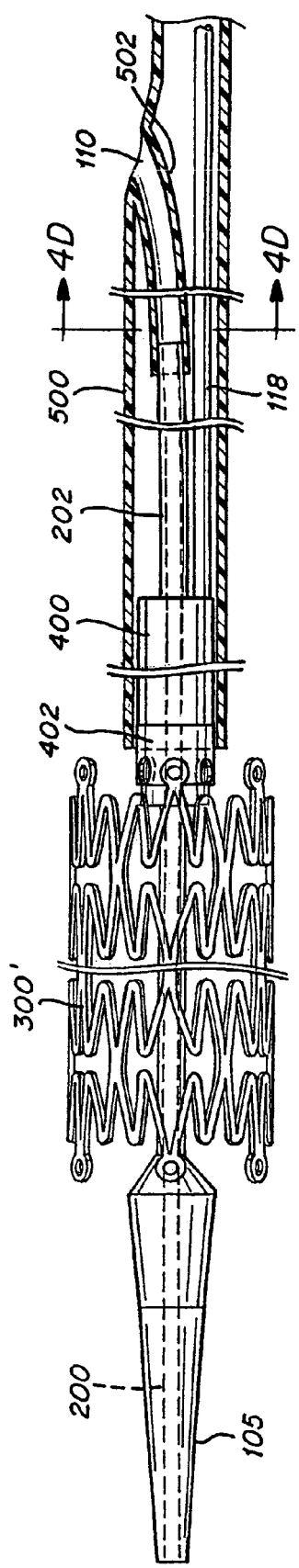
Figure 4D:
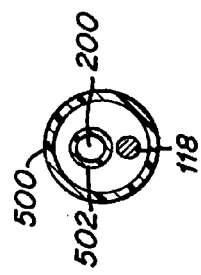
FIG. 4D is a cross-sectional view of a portion of the delivery system shown in FIG. 4C as taken along line 4D-4D.

Similar to the operation of the delivery system, as is known, when the interlocking outer member 500 is withdrawn proximally of the interlocking inner member 400, as shown in FIG. 4C, the interlocking stent 300' will expand and release from the interlock mechanism 402. Once the interlocking outer member 500 has been pulled back past the interlocking mechanism 402, the interlocking stent 300' is fully released from the inner member 400 for placement in the patient's lumen. Similar to the operation as described in U.S. Pat. No. 6,623,518, while the interlocking outer member 500 has not been pulled back past the interlock mechanism 402, the interlocking stent 300' can be adjusted as to its desired placement location in the patient's lumen.

The lengths of the guidewire lumen extension 202 and the RX port extension 502 are chosen such that, even when the interlocking outer member 500 is moved, relative to the interlocking inner member 400, a distance which is greater than a length of the interlocking stent 300', the continuity of the guidewire lumen 200 is assured. The choice of the lengths of the guidewire lumen extension 202 and the RX port extension 502 provides the "telescoping" effect that maintains the continuity.

Figure 5:
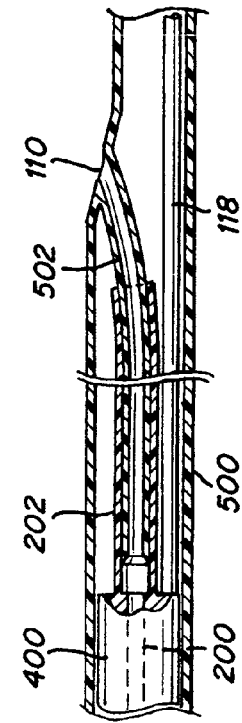
FIG. 5 is an alternate embodiment of the present invention.

In an alternate embodiment, the guidewire lumen extension portion 202 can be sized to receive the RX port extension 502 within, as shown in FIG. 5.

Figure 6:
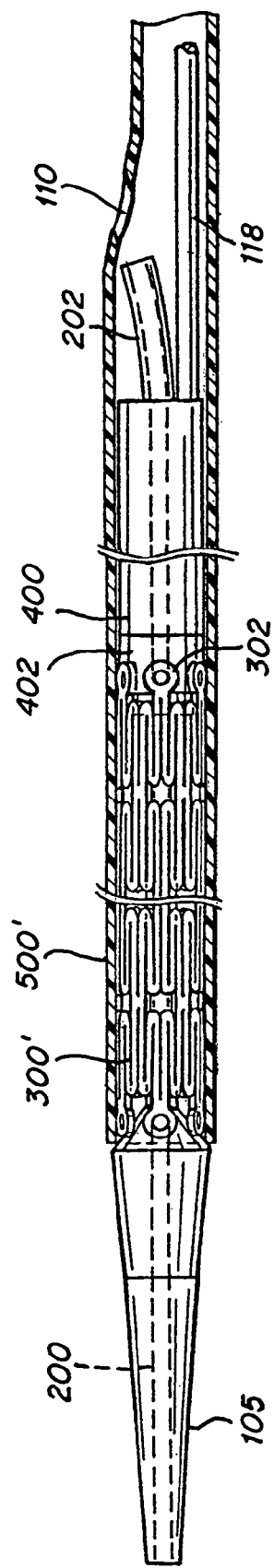
FIG. 6 is an alternate embodiment of the system as shown in FIG. 4B.

In an alternate embodiment to that which is shown in FIG. 4B, an interlocking outer member 500' is provided without the RX port extension 502, as shown in FIG. 6. Once the guidewire lumen extension portion 202 is oriented to direct a guidewire 106 (not shown) to the RX port 110, the pressure of the interlocking stent 300' will maintain the orientation during normal handling of the system.

In another embodiment of the present invention, the RX port 110 is positioned as a proximal opening in an interlocking outer member 500'' as shown in FIG. 12. The interlocking outer member 500'' is shaped such that the RX port 110 is positioned at a proximal end of the outer member 500'' and the guidewire lumen extension 202 is oriented to direct a guidewire 106 (not shown) to the RX port 110, where the pressure of the interlocking stent 300' maintains the orientation during normal handling of the system. The positioning of the RX port 110 at a proximal portion of the outer member 500'' differs, for example, from the placement of the RX port 110 as a "skive" in the outer member 500' as shown in FIG. 6.

As shown in FIG. 10, a delivery system 1000 in accordance with another embodiment of the present invention comprises a bitumen construction. An RX port lumen 1002 and a push wire lumen 1004 are provided within an interlocking outer member 1005. The interlocking outer member 1005 is joined to bitumen tube 1008 at joint region 1009 using adhesives, heat bonding, or other means as are known in the art. The RX port lumen 1002 receives the guidewire lumen extension portion 202 to direct a guidewire (not shown) to the RX port 110. The RX port 110 may comprise a skive in the side of the interlocking outer member 1005 or an opening in a proximal portion, similar to the embodiment shown in FIG. 12. The push wire lumen 1004 receives the push wire 118. A cross-section of the delivery system taken at line 11-11 is shown in FIG. 11. As the outer member 1005 moves with respect to the inner member 400, the guidewire lumen extension portion 202 moves within the RX port lumen 1002 to maintain the guidewire through the RX port 110.

As shown in FIG. 10, two spacers 1006 are provided on the push wire 118 to prevent entanglement between the push wire 118 and the guidewire lumen extension 202. The spacers 1006 can be made of a flexible polymer such as polyethylene, nylon, PEBAX, polyester, and the like. The spacers 1006 can be attached to the push wire 118 using an adhesive, by being heat bonded, ultrasonically bonded, or any other suitable method as is known in the art. In one embodiment, the spacers 1006 are polyester heat shrink. In a typical application, the spacers 1006 are 2 cm long and two are provided on the push wire 118 with a space between them in the range of 5-8 cm. One of ordinary skill in the art will understand that the number of spacers, their sizes and the distance between them in order to prevent entanglement between the push wire 118 and the guidewire lumen extension portion 202 is determined by the geometry of the system. The number shown and the dimensions provided are for explanatory purposes only and not meant to be limiting.

Alternatively, the spacers 1006 can be placed on the guidewire lumen extension 202 instead of the push wire 118. Further, spacers 1006 may be provided on each of the guidewire lumen extension portion 202 and the push wire 118 to prevent entanglement between them. One of ordinary skill in the art will understand that the spacers 1006 must be sized and positioned so as not to interfere with the operation of the device and yet still prevent entanglement.

One of ordinary skill in the art will understand that any one of a number of geometries as between the interlocking stent 300' and the interlocking mechanism 402 can be used. Certain geometries and concepts can be found in, for example, U.S. Pat. No. 6,623,518 and adapted for use in the embodiments disclosed herein.

Figure 7:
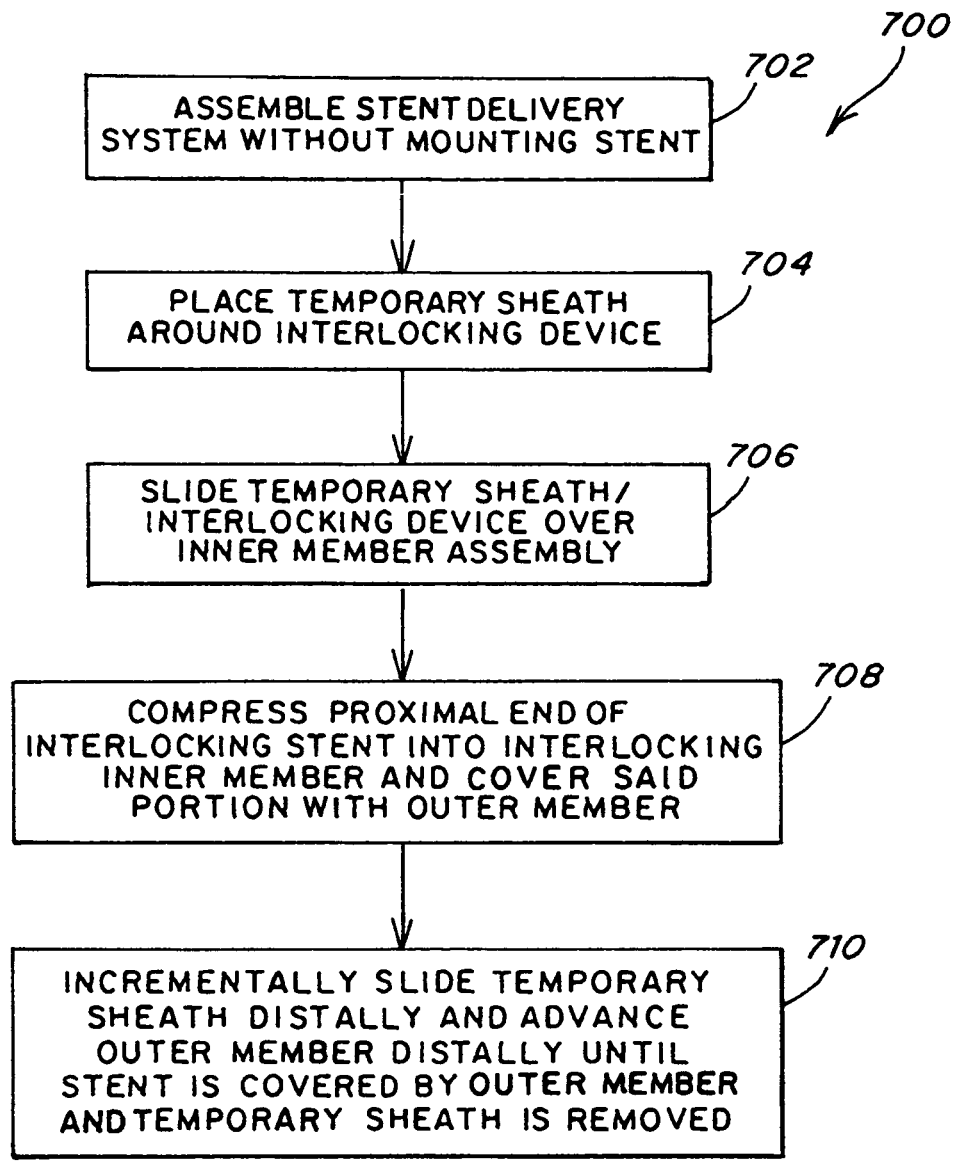
FIG. 7 is a flowchart outlining the steps in making a system according to one embodiment of the present invention.

An assembly method (700) of an implant delivery system according to the present invention is described with respect to the flowchart of FIG. 7. Initially, a stent delivery system 100 is completely assembled, except for the mounting of the stent on the system (702). Next, a temporary sheath, of a material strong enough to maintain the stent 300' in its compressed state and yet thin, is placed around the stent (704). The outer member of the stent delivery system is withdrawn proximally and the temporarily sheathed stent is slid over the inner member assembly (706). The proximal end region of the stent is next engaged with the interlock mechanism 402 of the interlocking inner member 400 and the interlocking outer member 500, 500' is advanced distally to cover the proximal end region of the stent (708). The sheath maintains the stent at a compressed diameter that is secure in the interlock mechanism 402. Finally, the temporary sheath is incrementally advanced distally while the outer member is also incrementally advanced distally until the temporary sheath is entirely removed from the stent and the outer member covers the entire length of the stent (710).

The interlocking outer member 500 may be made of a clear or translucent material to allow an operator to visually identify when the RX port is properly oriented or aligned. In one embodiment, one or the other or each of the interlocking inner member 400 and the interlocking outer members 500 or 500' may be provided with one or markings to aid in the orienting operation. Still further, a guidewire 106 may be inserted through the guidewire lumen 200 or RX port 110 to assist with the alignment operation.

As the temporary sheath is removed 710, allowing the interlocking stent 300' to expand, such expansion provides the pressure or friction fit with the interlocking outer member 500 that maintains the alignment of the system. During normal handling and operating conditions, the guidewire lumen 200 remains aligned with the RX port 110. Advantageously, the interlocking inner member 400 and interlocking outer member 500 can still be moved with respect to one another in order to deliver the medical implant, i.e., the stent 300'.

Another advantage of the invention, and especially those in embodiments shown in FIGS. 10, 11, 4A-C and 5 is that the volume of air in the catheter is reduced compared to prior art designs. Air in the catheter must be removed prior to introducing the catheter into the vasculature, for various reasons, but particularly to reduce the likelihood of air embolism. Air embolism is well known to be undesirable in most vascular beds and potentially fatal in the coronaries.

Air is removed from catheters using techniques well-known in the art. Typically, a syringe, and optionally a needle, is used to flush a fluid, such as saline, through the catheter to displace the air. In the catheters of the present invention, air may be removed by flushing the guidewire lumen 200 from the distal port 108 through RX port 110. However, this technique, and others common in the art, does not effectively remove air from the volume external to the inner member 104 and internal to the outer member 102. Consequently, when a stent is released by retracting the outer member proximally relative to the inner member, the air in this volume can be released into the patient, causing air embolism.

It is particularly important to minimize the amount of air left in the distal portion of the catheter, for example in the region distal to RX port 110, because air in this location has the greatest potential to embolize. In the illustrative embodiments, the clearances between a compressed stent and and inner member 104 in the region of the stent receiving portion 204 are minimized, as are the clearances between the outer diameter of guide wire lumen extension 202 and the mating, telescoping inside diameter of outer member 500'. In one example, the inventive system may have a calculated air volume in the outer member distal to RX port 110 (excluding the air volume of the guidewire lumen 200) of approximately 0.002 cubic centimeters while previously known competitive devices may have a similarly calculated air volume approximately 0.017 cubic centimeters.

While the various embodiments of the present invention have related to stents and stent delivery systems, the scope of the present invention is not so limited. For example, while particularly suited for stent delivery systems, it will be appreciated that the various aspects of the present invention are also applicable to systems for delivering other types of self-expandable implants. By way of non-limiting example, other types of self-expanding implants include anastomosis devices, blood filters, grafts, vena cava filters, percutaneous valves, atrial appendage closure devices, septal defect closure devices, or other devices.

Further, while choices for materials and configurations may have been described above with respect to certain embodiments, one of ordinary skill in the art will understand that the materials described and configurations are applicable across the embodiments. Thus, for example, the axial ridges 901 may be implemented in multiple embodiments described above.

What is claimed is:

1. A system for delivering a self-expanding implant within a body lumen comprising:
   a tubular catheter having proximal and distal ends and comprising an outer shaft member slidably disposed about an inner shaft member, the inner shaft member having a first interlock structure;
   a tubular self-expanding implant disposed intermediate the inner and outer shaft members, a proximal end of the implant having a second interlock structure configured to mate with the first interlock structure to maintain rotational alignment between the implant and the inner shaft member;
   a guide wire lumen extending at least partially through the inner shaft member from a proximal opening to a distal opening in the inner shaft member and exiting the outer shaft member through a radial guide wire lumen opening of the outer shaft member at a location intermediate of the catheter proximal end and the proximal opening in the inner shaft member; and
   an alignment mechanism comprising a contact surface disposed about an inner circumference of the outer shaft member, said inner circumference being in frictional contact with at least a portion of the self-expanding implant to maintain rotational alignment of the outer shaft member relative to the inner shaft member, thereby maintaining alignment between the guide wire lumen and the guide wire lumen opening.

2. The system of claim 1 wherein the proximal end of the self-expanding implant is releasably coupled to the inner shaft member.

3. The system of claim 2 wherein the self-expanding implant has tab portions which releasably engage with the first interlock structure disposed on the inner shaft member.

4. The system of claim 1 wherein the alignment mechanism further comprises:
   a tubular inner shaft extension coupled to the guide wire lumen and extending proximally from the proximal opening in the inner shaft member.

5. The system of claim 4 wherein the alignment mechanism further comprises:
   an outer shaft extension extending distally from the radial guide wire lumen opening radially inwardly at least partially through the outer shaft member and slidably engaging with the tubular inner shaft extension so as to prevent rotation between the inner shaft member and the outer shaft member.

6. The system of claim 5 wherein the outer shaft extension is tubular and slidably disposed about the tubular inner shaft extension for longitudinal movement therebetween.

7. The system of claim 6 wherein a length of the tubular inner shaft extension encompassed by the tubular outer shaft extension defines a usable length of longitudinal movement between the inner shaft member and the outer shaft member while preventing rotation therebetween.

8. The system of claim 6 wherein the inner shaft extension has an outer diameter less than an inner diameter of the outer shaft extension.

9. The system of claim 1, further comprising a plurality of axial ridges extending from an inner surface of the outer shaft member, the axial ridges releasably directly engaging the proximal end of the self-expanding implant, thereby maintaining rotational alignment of the outer shaft member relative to the inner shaft member.

10. A system for delivering a medical device within a body lumen comprising:
    a tubular inner shaft member having a proximal end and a distal end and an inner shaft guide wire lumen radially offset from a center axis of the tubular inner shaft member and extending at least partially therethrough, and a guide wire extension tube extending proximally from the proximal end of the tubular inner shaft member;
    a tubular outer shaft member having a proximal end and a distal end and defining an outer shaft guide wire lumen extending at least partially therethrough and a guide wire opening disposed in a sidewall of the outer shaft member at a location proximal of the distal end of the outer shaft member, the outer shaft guide wire lumen being radially offset from a center axis of the tubular outer shaft member and slidably receiving the guide wire extension tube, the outer shaft member being slidably disposed about the inner shaft member;
    a push wire connected to the proximal end of the tubular inner shaft member for slidably moving the tubular inner shaft member in the tubular outer shaft member; and
    a self-expanding medical device disposed intermediate the inner and outer shaft members in a compressed configuration, a first end of the medical device having tab portions releasably coupled to an interlock mechanism disposed on the inner shaft member to maintain rotational alignment between the medical device and the inner shaft member, the compressed medical device being in friction contact with an inner surface of the outer shaft member, the friction contact between the medical device and the outer shaft member maintaining rotational alignment between the guide wire extension tube and the outer shaft guide wire lumen.

11. The system of claim 10 wherein the guide wire extension tube has an outer diameter less than an inner diameter of the outer shaft guide wire lumen.

12. The system of claim 10 wherein a length of the guide wire extension tube and a length of the outer shaft guide wire lumen are sized so that the guide wire extension tube remains slidably disposed within the outer shaft guide wire lumen during relative movement between the outer shaft member and the inner shaft member.

13. The system of claim 10, further comprising:
a contact surface disposed about an inner circumference of the outer shaft member, said surface in contact with at least a portion of the medical device, said contact maintaining rotational alignment of the outer shaft member relative to the inner shaft member.

14. The system of claim 13 wherein the contact surface further comprises:
a plurality of axial ridges disposed along the inner circumference of the outer shaft member.

15. The system of claim 13 wherein the medical device comprises a tubular self-expanding stent having first and second ends.

16. The system of claim 15 wherein a first end of the self-expanding stent frictionally engages the contact surface on the inner circumference of the outer shaft member.

* * * * *